United States Patent [19]

Federman et al.

[11] Patent Number: 5,318,011
[45] Date of Patent: Jun. 7, 1994

[54] IRIS PROTECTOR/DILATOR AND METHOD OF USING THE SAME

[75] Inventors: Jay L. Federman, Philadelphia; Kenneth P. Cook, Blue Bell, both of Pa.

[73] Assignee: Escalon Ophthalmics, Inc., Skillman, N.J.

[21] Appl. No.: 831,129

[22] Filed: Feb. 4, 1992

[51] Int. Cl.$^5$ .............................................. A61B 17/02
[52] U.S. Cl. ..................................... 128/20; 606/107; 606/192; 623/4
[58] Field of Search ................ 606/107, 166, 192–196; 128/20, 898; 623/4–6

[56] References Cited

U.S. PATENT DOCUMENTS

| | | |
|---|---|---|
| 2,754,520 | 7/1956 | Crawford . |
| 2,812,758 | 11/1957 | Blumenschein . |
| 3,454,966 | 7/1969 | Rosen ..................................... 623/6 |
| 3,490,455 | 1/1970 | Illig . |
| 3,925,825 | 12/1975 | Richards et al. ........................ 623/6 |
| 4,037,589 | 7/1977 | McReynolds . |
| 4,206,518 | 6/1980 | Jardon et al. ............................ 623/6 |
| 4,257,406 | 3/1981 | Schenk . |
| 4,275,733 | 1/1981 | Marinoff . |
| 4,321,916 | 3/1982 | McKee . |
| 4,387,706 | 6/1983 | Glass . |
| 4,449,257 | 5/1984 | Koeniger ................................. 623/6 |
| 4,452,235 | 6/1984 | Reynolds . |
| 4,782,820 | 11/1988 | Woods . |
| 4,919,662 | 4/1990 | Knoll et al. ............................. 623/6 |
| 4,991,567 | 2/1991 | McCuen et al. . |
| 4,993,936 | 2/1991 | Siepser . |
| 5,163,419 | 11/1992 | Goldman ................................ 128/20 |

FOREIGN PATENT DOCUMENTS 0766596  9/1980  U.S.S.R. ............................... 128/898

*Primary Examiner*—Richard J. Apley
*Assistant Examiner*—Donna L. Maraglio
*Attorney, Agent, or Firm*—Panitch Schwarze Jacobs & Nadel

[57] ABSTRACT

An iris dilator includes a body formed of an expansile material being expandable from a dehydrated first size and shape to a hydrated second size and shape. When hydrated, the dilator has a shape complementary to an inside diameter of the iris and a size sufficient to dilate the iris. In addition, a mammalian iris may be dilated by inserting the at least partially dehydrated iris dilator described above into a position radially inwardly from the iris where, in the presence of bodily or surgical fluids, the dilator hydrates and expands to engage and dilate the iris. An apparatus for deforming the dilator to facilitate insertion in use includes top and bottom surfaces which engage top and bottom sides of the dilator, respectively, at least one depression member for forming a depressed area on an edge of the dilator and at least one retainer member for retaining a non-depressed area on the edge of the dilator.

12 Claims, 4 Drawing Sheets

IRIS PROTECTOR/DILATOR AND METHOD OF USING THE SAME

FIELD OF THE INVENTION

The present invention relates to an intraoperative iris dilator apparatus for use in mammals and to a method for forming and inserting the dilator into the mammalian eye.

BACKGROUND OF THE INVENTION

Surgical procedures invariably involve a certain amount of trauma to tissues and organs at and around the surgical site. Minimizing surgical trauma is an important goal because it helps to minimize the risk of complications and helps reduce the postsurgical healing period. Trauma is of particular concern in surgical procedures involving the eye because of the delicate nature of that organ and its constituent parts.

Several surgical procedures in the eye involve entering the eye through a small incision through the cornea or front of the eye and proceeding past the plane of the iris and through the pupil. Cataract removal and implantation of a replacement lens, such as an intraocular lens, is one example of such a procedure.

To avoid injury to the iris, a critical but weak and delicate organ controlling the amount of light entering the eye, in procedures passing through or near the iris, it is desirable to dilate the pupil to keep the iris out of harm's way and to give the surgeon a wider opening through which to work and view the posterior segments of the eye. During an eye surgery procedure, the eye surgeon may dilate the iris chemically using a mydriatic. However, this dilation method is limited in time and offers no protection to the iris against the invasive procedures.

Mechanical dilators or retractors have also been developed. For example, U.S. Pat. No. 4,387,706 discloses an iris retractor comprising a substantially circular, resilient ring which is compressed or deformed while inserting through an incision in the cornea, where it is then worked into an abutting relationship with the iris, where compression forces are released to allow the retractor to return to its normal (expanded) shape, forcing the iris open. U.S. Pat. No. 4,782,820 discloses an adjustable iris retractor which preferably has a pair of separable, slideably interengaged ends which allows sliding movement to increase or decrease the diameter of the retractor. U.S. Pat. Nos. 3,490,455; 4,037,589; 4,257,406; and 4,991,567 disclose various conventional clamps, tacks and mechanical devices typical of other conventional retractors used in a variety of surgical procedures. Such conventional mechanical dilators and retractors are expensive to manufacture, cumbersome to use, traumatic to the iris, and often require large incisions for insertion and use.

In view of the deficiencies of the prior art, it would be desirable to have a mechanical iris dilator, which is easy to manufacture and is easy and safe to use.

BRIEF SUMMARY OF THE INVENTION

According to the present invention, an iris protector/dilator ("dilator") comprises a body formed of an expansile material being expandable from a dehydrated first size and shape to a hydrated second size and shape. When hydrated, the dilator has a shape complementary to an inside diameter of the iris and a size sufficient to dilate the iris.

In addition, the present invention is directed to a method for dilating a mammalian iris, comprising inserting an at least partially dehydrated iris dilator into a position radially inwardly from the iris, where, in the presence of bodily or surgical fluids, the dilator hydrates and expands to engage and dilate the iris.

Further according to the present invention, an apparatus for deforming the iris dilator from the hydrated second size and shape to the dehydrated first size and shape comprises top and bottom surfaces for engaging the top and bottom sides, respectively, of the iris dilator, at least one slidingly movable depression member for engaging and forming a depressed area of the dilator edge and at least one slidingly movable retainer member for engaging and retaining a non-depressed area of the dilator edge. Methods of manufacturing the iris dilator of the present invention and deforming the same during dehydration to facilitate insertion into the eye are also part of the present invention.

BRIEF DESCRIPTION OF THE DRAWINGS

The foregoing summary of the invention, as well as the following detailed description of preferred embodiments, will be better understood when read in conjunction with the appended drawings. For the purpose of illustrating the invention, there are shown in the drawings embodiments which are presently preferred, it being understood, however, that the invention is not limited to the specific arrangements and instrumentalities disclosed. In the drawings.

DETAILED DESCRIPTION OF PREFERRED EMBODIMENTS

Figure 1:
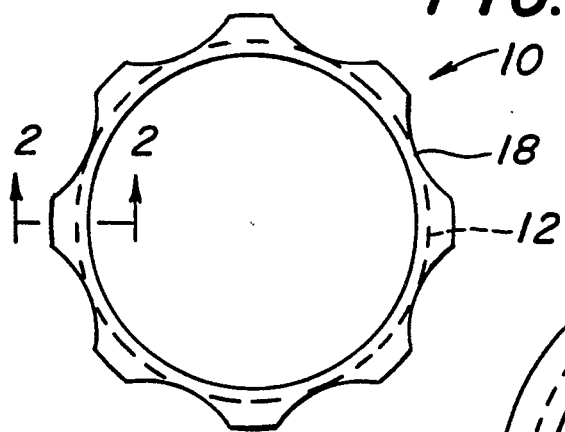
FIG. 1 is a top plan view of an iris dilator in accordance with the present invention.
Figure 2:
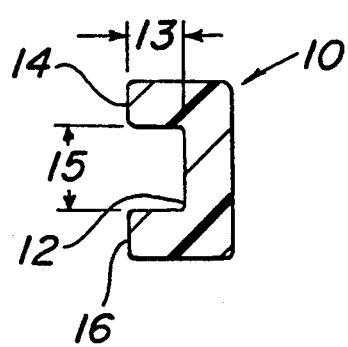
FIG. 2 is an enlarged cross-sectional view of the iris dilator along line 2—2 in FIG. 1.

Referring to the drawings, wherein like numerals indicate like elements throughout, there is shown in FIG. 1 an iris dilator 10 having a generally circular shape when in the presence of fluids normally found in the eye to conform to the shape of a typical iris. It is possible, however, to provide shapes other than circular where desired for differently shaped irises (such as those found in certain mammals). The iris dilator 10 is provided with an outwardly facing retaining groove 12 along the perimeter of the dilator as best shown in FIG. 2. The groove 12 should be shaped so as to receive and engage the inside edge of the iris while preferably at least partially enveloping the anterior and posterior surfaces of the iris for protection from surgical instruments and other objects and avoidance of irritation during surgery. Preferably, the retaining groove 12 has a generally block C-shape, as illustrated in FIG. 2, although one skilled in the art will appreciate that the iris dilator of the present invention may have grooves having other cross-sectional shapes, such as a U-shape, V-shape or Y-shape, for example.

The iris dilator according to the present invention is formed of an expansile material capable of decreasing in size to facilitate insertion when partially or completely dehydrated and increasing in size to dilate the iris when hydrated in the presence of water or other bodily or surgical fluid. Suitable materials having such qualities include hydrophilic polymer materials commonly called hydrogels or, in their hardened, compressed, dehydrated state, xerogels. Hydrogels possess a natural flexibility and memory of the material, which allows the hydrogel to be deformed or manipulated when hydrated but which is structurally strong enough to dilate a mammalian iris. While dehydrating the hydrogel, where deformation or manipulation forces are maintained, a compressed, generally hardened state results which maintains the deformed or manipulated shape without external forces.

At the same time, dehydration of hydrogels causes significant shrinkage. Conversely, rehydration of dehydrated hydrogels (xerogels) causes significant expansion of the material and, where deformed, a return to its original shape. The extent of shrinkage or expansion varies depending on the particular hydrogel material and its ability to hold fluid (fluid or water content). Presently preferred hydrogel materials include hydroxyethylmethacrylate (HEMA), and HEMA VP (vinyl pyrrolidone). Examples of suitable hydrogel materials, which may be used to form the dilator of the present invention include VISTA GEL available from Vista in England.

In its hydrated state, the iris dilator 10 should have an inner diameter large enough to achieve the dilation desired without over-dilating or placing undue force on the iris. While the extent of dilation desired and, hence, the desired diameter of the hydrated iris dilator 10, depends on the size of the individual iris, (which may vary from patient to patient), 7 mm or greater is a typical inner diameter dimension (when hydrated) for an iris dilator for a human eye.

When hydrated, the retaining groove 12 should have a width (dimension 15 in FIG. 2) large enough to allow the sides 14, 16 of the groove to extend radially inwardly from the edge of the iris (radially outwardly from the perimeter of the dilator 10) so as to at least partially envelop the anterior and posterior sides of the iris but not so wide as to allow the iris to collapse or fold. The depth (dimension 13 in FIG. 2) of the groove 12 should not be so large as to unnecessarily increase the size of the dilator, but should be deep enough when hydrated to hold and guide the iris in a dilated position. According to one presently preferred embodiment of the present invention, the groove 12 has a depth of about 0.010 inch and a width of about 0.014 inch although larger or smaller dimensions may be used depending on the particular dimensions of the iris to be dilated.

The iris dilator 10 of the present invention should have wall thicknesses large enough to be structurally stable in use but not so large as to impede use through relatively small incisions or to increase the time necessary for hydration to occur beyond the period of time desired for iris dilation to begin. Where the iris dilator 10 is formed of HEMA, the wall thicknesses are each about 0.008 inch, although larger or smaller thicknesses may be used depending on the material used to form the dilator and the size and resistance of the iris to be dilated.

The fabrication of the iris dilator 10 of the present invention may be done using conventional techniques and apparatus known in the art from a polymeric hydrogel material to the exact dimensions desired for the iris dilator. Fabrication is generally carried out in a dehydrated or xerogel state. Lathe cutting, machining, polishing, injection molding and other casting methods are suitable for such fabrication, but machining is presently preferred due to the small size of the dilator.

As discussed above, the nature of a hydrogel is such that, when hydrated, the hydrogel material expands in size. The extent of expansion is generally a factor of the fluid retaining capacity or water content of the hydrogel material. For example, a generally circular dehydrated hydrogel dilator formed in accordance with the present invention of HEMA having an inner diameter of about 5.5 mm expands, when substantially completely hydrated, to an inner diameter of about 8 mm.

Figure 3:
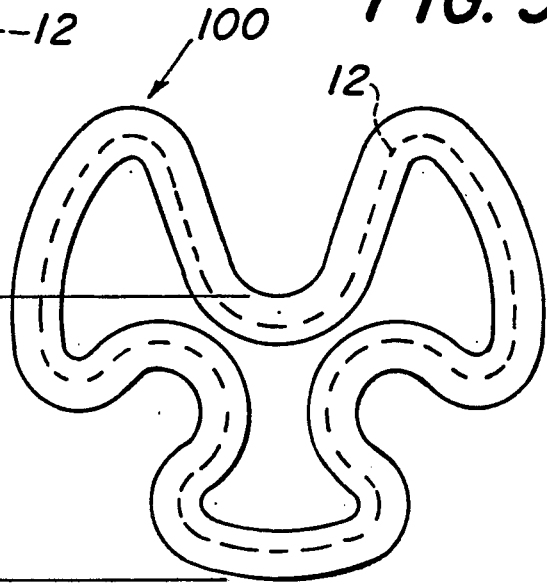
FIG. 3 is an enlarged diagrammatic view of an iris dilator in one possible deformed state for insertion according to the present invention.
Figure 11:
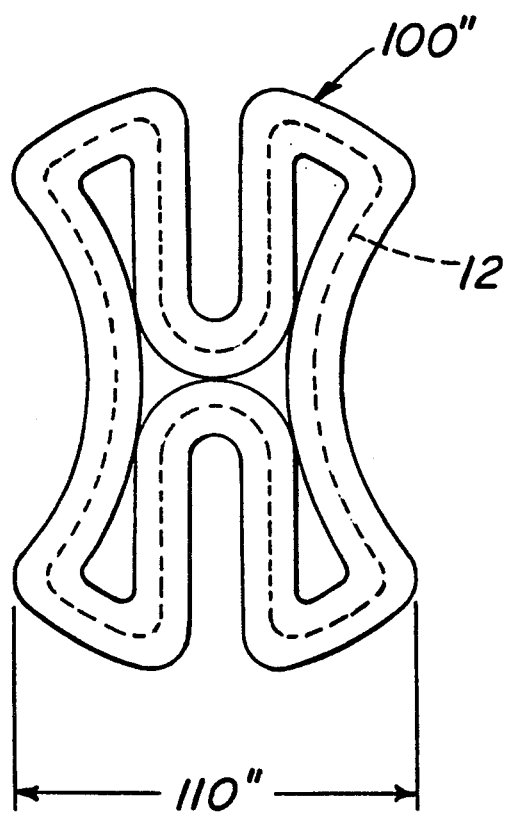
FIG. 11 is an enlarged diagrammatic view of an iris dilator in another possible deformed state for insertion as according to the present invention.

Further in accordance with the present invention, where it is desired to pass the iris dilator 10 through an incision having a size smaller than the diameter of the dehydrated hydrogel, it is preferred to compress and deform the hydrated hydrogel during dehydration to produce an iris dilator having a deformed shape capable of being passed through an incision of a predetermined size without regard to the size of the dilator. FIGS. 3 and 11 illustrate examples of deformed iris dilators having trilobal 100 and bilobal 100" shapes, which have been deformed in accordance with the present invention, although it will be understood that other shapes are possible and may be desirable depending, in part, on the shape, size and/or location of the incision through which the dilator is to be inserted.

Figure 5:
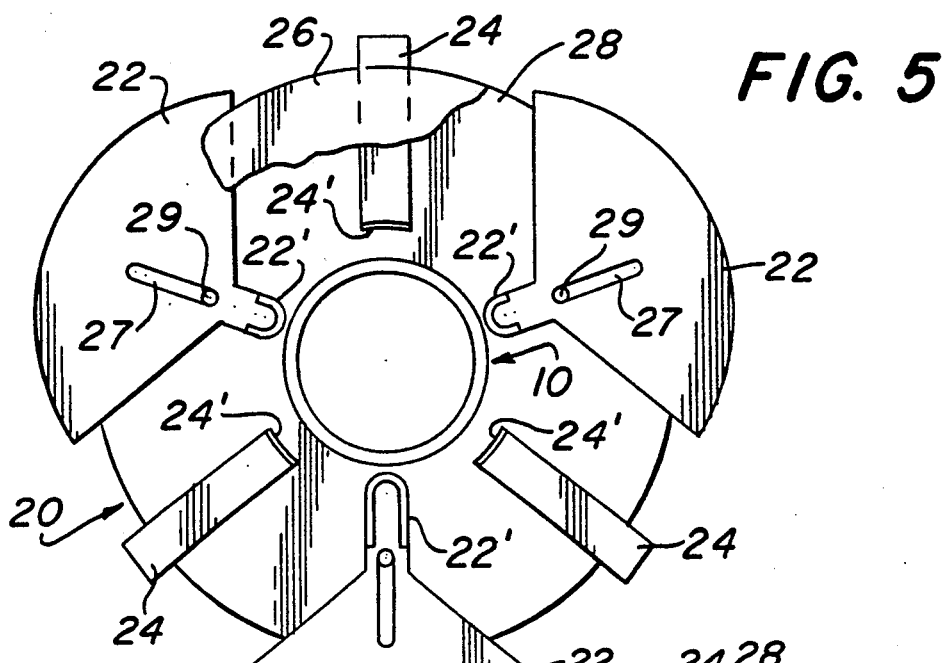
FIG. 5 is a partially broken away top plan view of an iris dilator deforming apparatus in accordance with the present invention showing the iris dilator deforming apparatus in a fully open position and the iris dilator in a non-deformed state.
Figure 6:
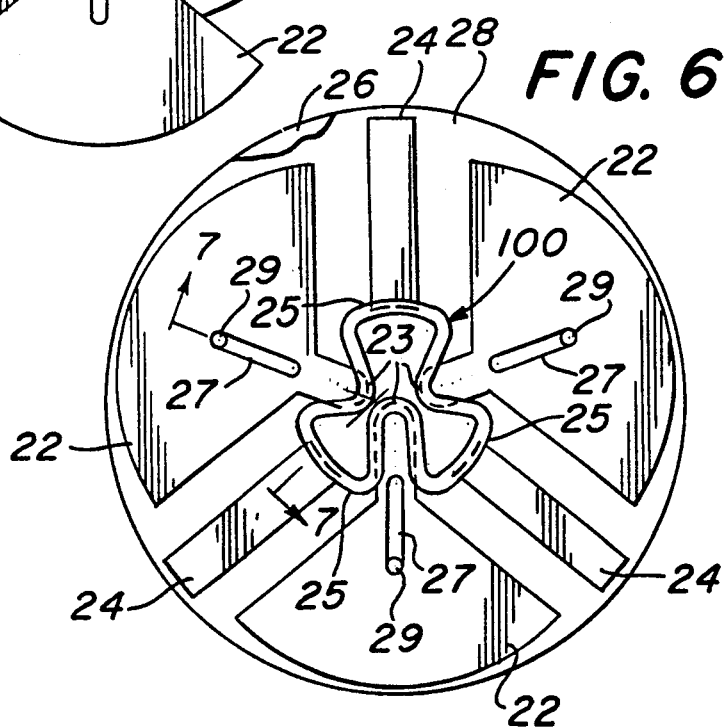
FIG. 6 is a top plan view of the iris dilator deforming apparatus illustrated in FIG. 5 at a later stage of deformation.
Figure 8:
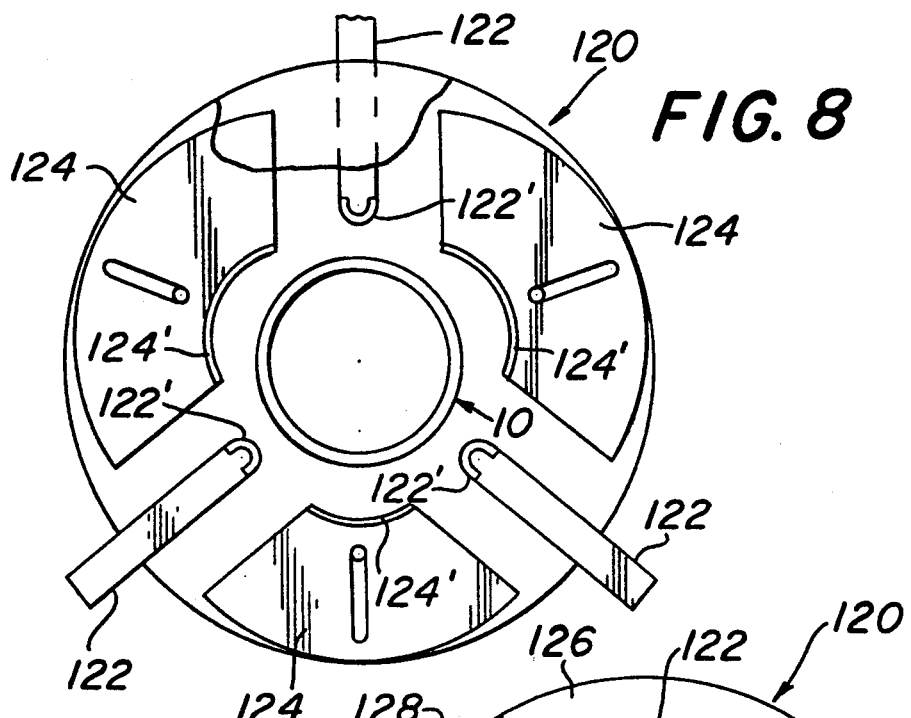
FIG. 8 is a partially broken away top plan view of another iris dilator deforming apparatus in accordance with the present invention showing the iris dilator deforming apparatus in a fully open position and the iris dilator in a non-deformed state.
Figure 9:
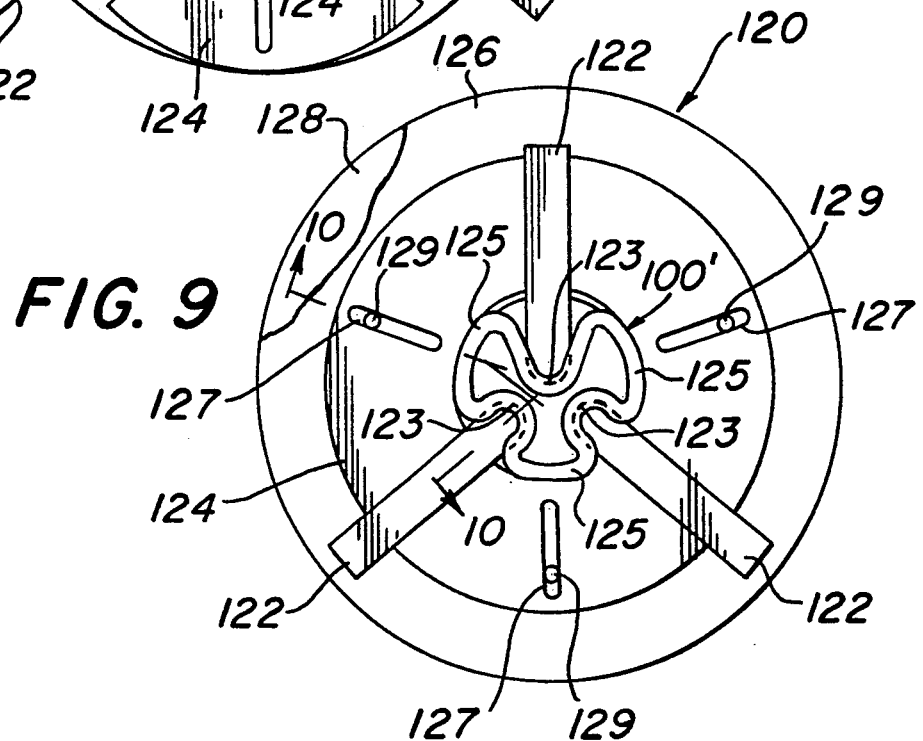
FIG. 9 is a top plan view of the iris dilator deforming apparatus illustrated in FIG. 8 at a later stage of deformation.

Beginning with a hydrated iris dilator 10, the dilator is deformed into a desired shape while dehydration due to evaporation is allowed to occur. Evaporation may be enhanced, for example, by heating and/or passing air over the iris dilator. Deformation may be facilitated using a deformation apparatus, such as that according to the present invention. Referring to FIGS. 5 and 8, a deformation apparatus 20, 120 for deforming an iris dilator to the shape of FIG. 3 comprises depression bars 22, 122 which may be moved radially inwardly as illustrated in FIGS. 6 and 9 to engage the groove 12 of the dilator 10 to cause depressions 23, 123 in the previously circular (or other original) shape of the iris dilator 10. Because hydrogels tend to be elastic and slippery, retainer segments 24, 124 are also provided to prevent the non-depressed areas 25, 125 of the iris dilator 10 from slipping away from the depression bars 22, 122. The depression bars 22, 122 and retainer segments 24, 124 are preferably provided with projections (22′, 24′ and 122′, 124′) having a shape that substantially complements the groove 12 of the dilator 10 to facilitate engagement and positioning by the deforming apparatus 20, 120 of the dilator 10.

Figure 7:
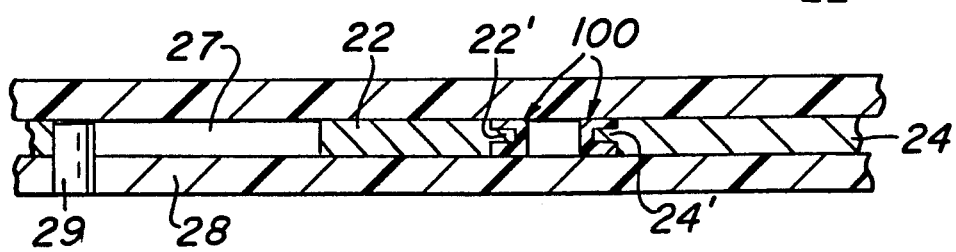
FIG. 7 is a partial cross-sectional view of the apparatus and dilator along line 7—7 in FIG. 6.
Figure 10:
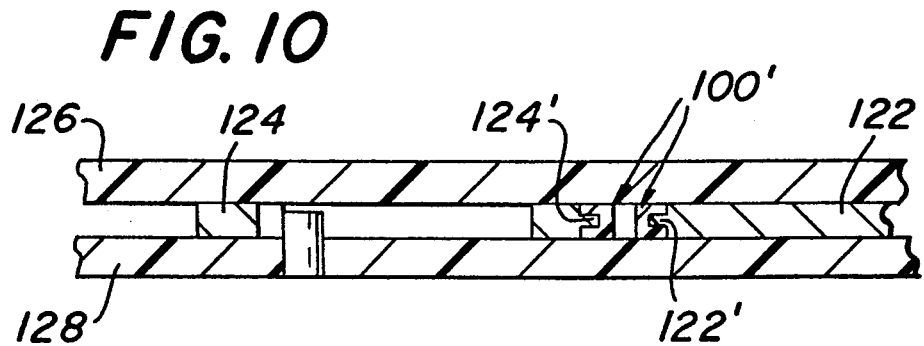
FIG. 10 is a partial cross-sectional view of the apparatus and dilator along line 10—10 in FIG. 9.

Moreover, to prevent vertical slippage of the iris dilator 10 (i.e., popping out of the plane of the apparatus 20, 120), a top side (cover) support 26, 126 and a bottom side support 28, 128 may be supplied as best illustrated in FIGS. 7 and 10 each having a surface which engages a side of the dilator to hold it in the desired plane. Such top and bottom side supports may be formed of transparent materials to facilitate viewing of the deformation and dehydration processes. To facilitate dehydration, the side supports may be supplied with holes (not shown) through which air may pass or be forced.

As the iris dilator 10 dehydrates under the deformation forces of the depression bars 22, 122 and retainer segments 24, 124, the bars and segments may be repositioned periodically as the dilator shrinks in size. Positioning and repositioning may be facilitated by providing means to slide the depression bars 22, 122 radially inwardly, such as the pin 29, 129 and groove 27, 127 combination illustrated in FIGS. 5, 6, 7 and 8, 9, 10. The depression bars 22, 122, in turn, may be positioned to act as guides for sliding the retainer segments 24, 124 radially inwardly to deform the iris dilator 10. When dehydration is substantially complete, the now deformed iris dilator 100, 100′ may be removed from the deformation apparatus 20, 120.

Because of the nature of hydrogel materials, most dehydrated hydrogels are relatively rigid and will retain the shape in which it was dehydrated. Accordingly, once removed from the deformation apparatus 20, 120, the iris dilator 100, 100′, 100″ may be stored for later use. Aseptic packaging and storage techniques known in the art may be used to package and store the iris dilators.

Figure 4:
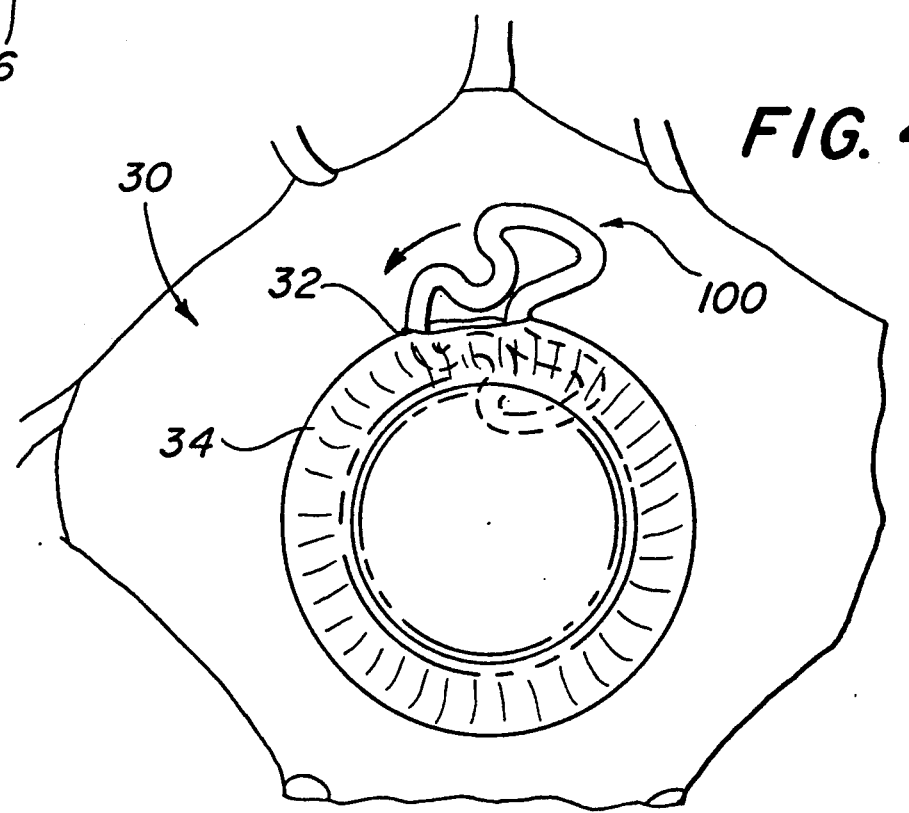
FIG. 4 is a top plan view showing surgical insertion in an eye of an iris dilator in the deformed state of FIG. 3.

To facilitate insertion of the iris dilator 10 of the present invention, it is presently preferred that the dilator is deformed in a manner which establishes an insertion width, which is smaller than the width of an incision in the patient's eye. For example, referring to FIG. 4, where a surgical procedure requires a 3 mm incision 32 in the eye 30, the insertion width 110 of the dehydrated iris dilator 100 should be less than 3 mm to allow easy insertion through the incision 32. A dehydrated iris dilator having a shape as illustrated in FIG. 3 may be inserted by rotating the dilator as it is inserted through the incision 32, as shown by the arrow in FIG. 4. A dehydrated iris dilator 100″ having a shape and width 110′ illustrated in FIG. 11 may be inserted without such manipulation.

To further facilitate insertion of the iris dilator 10 of the present invention, it may be desirable to partially rehydrate the dilator to soften the dilator, lessening any abrasive impact the dilator may have during the insertion procedure. However, it will be understood that the hydration process is difficult to control, and once the dilator begins hydrating (expanding), insertion and accurate positioning in the iris may become difficult.

Once inserted through an incision, the iris dilator of the present invention is positioned preferably radially inwardly from the iris 34 so that the iris dilator 10 engages the iris 34 as the dilator expands and resumes its hydrated shape. Positioning hooks (not shown), such as lens positioning hooks, may be used where desired to help position the iris dilator relative to the iris. It will be readily appreciated by one of ordinary skill in the art in view of this disclosure that the iris dilator should be positioned so that the plane of the dilator lies substantially completely within the plane of the iris. As the iris dilator 10 expands and engages the iris, the dilator may be manipulated to ensure that the inner edge or periphery of the iris 34 enters the groove 12 of the dilator 10 for proper dilation (shown in phantom in FIG. 4) and protection of the iris.

The time necessary for rehydration of the iris dilator 10 to occur varies with the particular hydrogel material used and the thickness of such material. Preferably, therefore, as discussed above, the thickness of the iris dilator 10 is relatively thin. Moreover, it may be desired, although it is not necessary, to provide the iris dilator with holes (not shown) to increase the surface area of the dilator with respect to the rehydrating fluids. In addition, because the rate of rehydration of the iris dilator 10 of the present invention may not be uniform throughout the dilator structure, differential expansion may occur, causing buckling or twisting of the iris dilator during expansion. To minimize this problem, we have discovered that, by providing scallops 18 in the groove sides 14, 16, undesirable buckling can be minimized. While, for the sake of clarity, such scalloping is not illustrated in FIGS. 3 through 8, scalloping as illustrated in FIG. 1 is presently preferred and may be formed in the groove sides by machining, molding or other techniques described above.

The present invention may be embodied in other specific forms without departing from the spirit or essential attributes thereof and, accordingly, reference should be made to the appended claims, rather than to the specification, as indicating the scope of the invention.

We claim:

1. An iris dilator comprising a body formed of an expansile hydratable material, said material being expandable from a dehydrated first size and shape to a hydrated second size and shape when in the presence of bodily or surgical fluids, said body comprising a dehydrated dilator when said material is dehydrated, and a hydrated dilator when said material is hydrated, said hydrated dilator having a shape substantially complementary to an inside perimeter of a mammalian iris and having a size sufficient to dilate the iris when placed in substantial engagement with the iris, the hydrated dilator further having an aperture extending therethrough for permitting access through the natural opening of the iris, said body having a radially outwardly extending retaining groove along a perimeter thereof, said groove having side walls configured for at least partially enveloping anterior and posterior surfaces of the iris.

2. The iris dilator according to claim 1, wherein the material comprises hydroxyethylmethacrylate.

3. The iris dilator according to claim 1, wherein the dehydrated iris dilator body is substantially circular.

4. The iris dilator according to claim 3, wherein the iris dilator is provided with a centrally located aperture extending therethrough.

5. The iris dilator according to claim 1, wherein the hydrated dilator is substantially ring-shaped.

6. The iris dilator according to claim 5, wherein the hydrated dilator has an inner diameter of at least about 7 mm.

7. The iris dilator according to claim 1, wherein the side walls are scalloped-shaped.

8. The iris dilator according to claim 1, wherein said dehydrated dilator has a shape defining an insertion width allowing said dilator to be passed through a surgical incision of a predetermined size in a patient.

9. The iris dilator according to claim 8, wherein the insertion width is no larger than about 3 mm.

10. The iris dilator according to claim 8, wherein the dehydrated iris dilator has a bilobal shape.

11. The iris dilator according to claim 8, wherein the dehydrated iris dilator has a trilobal shape.

12. A method for dilating an iris of a mammalian patient using an iris dilator comprising a body formed of an expansile hydratable material, said material being expandable from a dehydrated first size and shape to a hydrated second size and shape when in the presence of bodily or surgical fluids, said body comprising a dehydrated dilator when said material is dehydrated, and a hydrated dilator when said material is hydrated, said hydrated dilator having a size sufficient to dilate a mammalian iris when placed in substantial engagement therewith, said hydrated dilator having a shape complementary to an inside perimeter of the iris, said hydrated dilator further having an aperture extending therethrough for permitting access through the natural opening of the iris, said body having peripheral walls configured for at least partially enveloping anterior and posterior surfaces of the iris, the method comprising the steps of:

(a) inserting the dehydrated iris dilator into a position radially inwardly from the iris;

(b) hydrating the iris dilator with bodily or surgical fluids;

(c) manipulating the iris dilator as it is being hydrated to ensure that it engages and dilates the iris.

* * * * *